(12) United States Patent
Willing

(10) Patent No.: US 6,437,865 B1
(45) Date of Patent: Aug. 20, 2002

(54) APPARATUS FOR THE MEASUREMENT OR VISUAL MATCHING OF THE COLOR OR COLOR EFFECTS OF SURFACES

(75) Inventor: Achim Willing, Schesslitz-Doschendorf (DE)

(73) Assignee: Dr.-Ing. Willing GmbH (DE)

( * ) Notice: Subject to any disclaimer, the term of this patent is extended or adjusted under 35 U.S.C. 154(b) by 0 days.

(21) Appl. No.: 09/406,020

(22) Filed: Sep. 24, 1999

(30) Foreign Application Priority Data

Sep. 25, 1998 (DE) .......................................... 198 44 053

(51) Int. Cl.[7] .................................................. G01J 3/46
(52) U.S. Cl. ....................................... 356/402; 356/244
(58) Field of Search ................................. 356/402, 421, 356/422, 423, 424, 425, 244; 362/33, 94, 97

(56) References Cited

U.S. PATENT DOCUMENTS 4,668,090 A * 5/1987 Kipphan et al. ............ 356/244

* cited by examiner

*Primary Examiner*—F. L. Evans
(74) *Attorney, Agent, or Firm*—Marshall & Melhorn, LLC

(57) ABSTRACT

An apparatus for the measurement or visual matching of colors and color effects on a flat or slightly curved sample is proposed, with a lighting apparatus, a sample support and an observer location, wherein the direction of observation of a sample is adjustable by translational displacement of the sample and in the process the lighting direction of the light which illuminates the sample surface remains constant to the sample surface.

9 Claims, 2 Drawing Sheets

APPARATUS FOR THE MEASUREMENT OR VISUAL MATCHING OF THE COLOR OR COLOR EFFECTS OF SURFACES

BACKGROUND OF THE INVENTION

1. Field of the Invention

The invention concerns an apparatus for the visual matching or alternatively for the contactless measurement of samples, wherein effects dependent on the direction of observation are to be detected as well.

2. Description of Related Art

Apparatuses for color measurement and for color matching are known, in ordinary color measurement starting from a sample which is fixed relative to the measuring device and which is illuminated from various predefined angles and usually observed perpendicularly to the surface. In these apparatuses, the measuring devices are arranged in the immediate vicinity of the sample surface and only very small surface portions are viewed. For the color matching of smaller samples, small lighting booths are usual, e.g. table-mounted booths, in which is provided a stationary lighting system for illumination of the samples. In order to detect the different color effects, the sample surfaces, usually a sample to be measured and a reference sample, are presented to an observer from different angles and so also illuminated from different angles. This method has the drawback of poor reproducibility, because both the lighting angles and the angles of observation change in different observation situations, in particular color effects are difficult to detect, and moreover only very small samples can be matched.

From U.S. Pat. No. 5,604,586 is known an apparatus for color matching which comprises a concavely shaped plate for receiving a sample to be matched. Furthermore there is provided a sample holder for a reference sample, which is also concavely curved and which is pivotable about a common evolute of the surface of the plate and the surface of the sample holder. Above the samples is arranged a surface lighting apparatus whose radiating surface is convex and which irradiates the samples with uniform and diffuse light of predetermined intensity.

OBJECT OF THE INVENTION

It is the object of the invention to find an apparatus for measurement or visual matching for small and medium-sized flat or slightly curved samples, which allows reproducible and clearly defined, different observation conditions with sufficiently similar lighting conditions, and which under the same conditions is suitable both for visual matching and for color measurements.

This object is achieved according to the invention by the characteristics of the main claim.

SUMMARY OF THE INVENTION

The apparatus according to the invention starts from a fixed observer location. From this location a surface element on the sample or the assembly of several samples is viewed at their edges adjoining each other, preferably in a basic position from the direction of the normal of the surface element. By the position of the sample is fixed a plane in which the sample is located. A change in the angle of observation is caused according to the invention by the fact that the sample is displaced in a linear direction until the desired angle of observation is reached as the angle between the direction of observation and the normal on the sample or surface element. According to the usual stipulations in many color matching regulations, the sample is illuminated in its basic position in the usual manner obliquely, preferably at 45°. This can be done by an almost parallel or narrowly focused beam path, e.g. with spotlights and parabolic reflectors. Particularly advantageous, however, and with a high correlation with the lighting conditions outdoors, is a beam path which is narrowly focused only in a main plane. Light distribution of this kind can be produced by linear light sources.

According to the invention the whole surface in which the sample or portions of the sample can be located is now illuminated at each location from the same oblique direction. This means that the lighting conditions on the sample remain constant even in case of displacement, with the result that reproducible matching dependent on the angle of observation is guaranteed.

When using linear light sources, the main plane of radiation in which maximum focusing is achieved is the plane which contains the normal on the sample and the straight line of displacement of the sample. The longitudinal axes of the lamps or light sources run perpendicularly to this main plane. If the sample is arranged vertically and displaced horizontally, the result is therefore vertically oriented lamps parallel to the sample. If the sample is likewise arranged vertically but displaced vertically, the result is horizontally oriented lamps parallel to the sample. These can be mounted for example on the ceiling or on side walls.

The lamps, if necessary with appropriate filtering, are selected in particular for visual matching such that their spectral distribution meets preset conditions, e.g. a color temperature of 6500 K and high enough index of metamerism in daylight. This is provided for example by certain fluorescent tubes.

With the same geometry, according to the invention the observer's eye can be replaced by a sensor optical system, whose optical system spectrally assesses the beam density of the sample.

BRIEF DESCRIPTION OF THE DRAWINGS

Practical examples of the invention are shown in the drawings and described in more detail in the description below. They show.

DESCRIPTION OF THE PREFERRED EMBODIMENT

Figure 1:
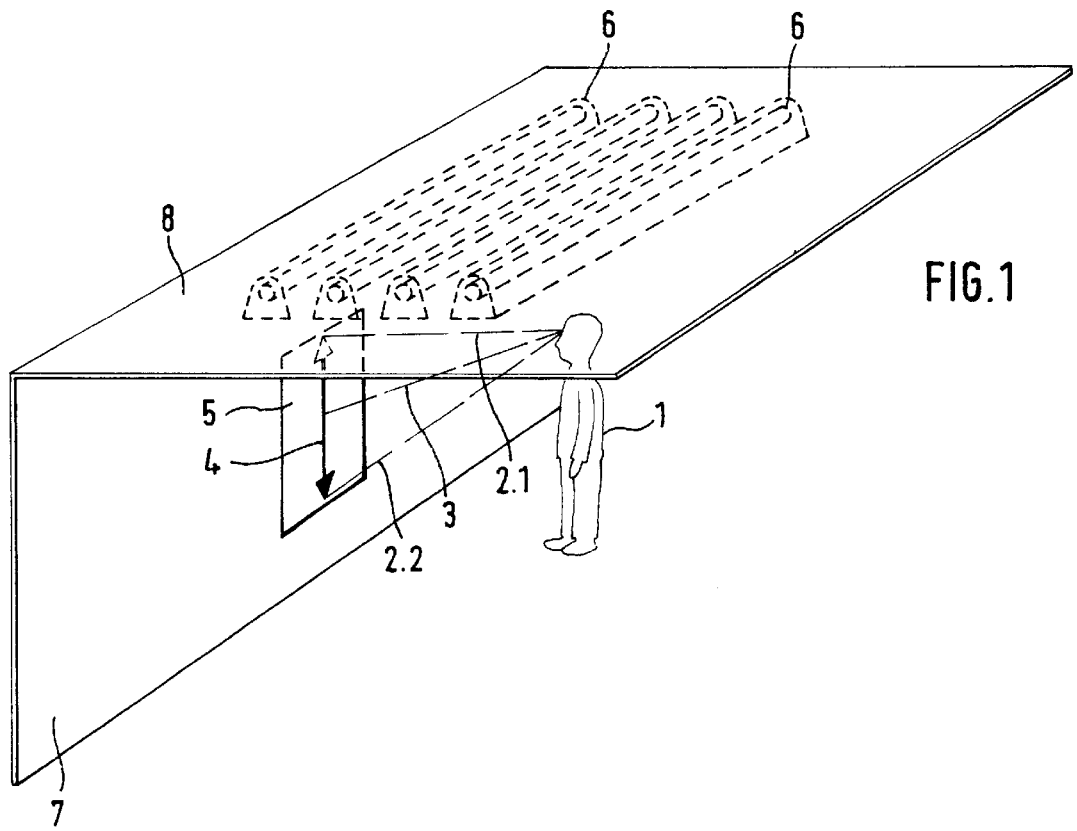
FIG. 1 a perspective view of the arrangement according to the invention which can be realized as a light booth, with vertical displacement of the sample, FIG. 2 a vertical section through the arrangement according to FIG. 1, FIG. 3 a perspective view of the arrangement according to the invention, with horizontal displacement of the sample, and FIG. 4 a top view of the arrangement according to FIG. 3.
Figure 2:
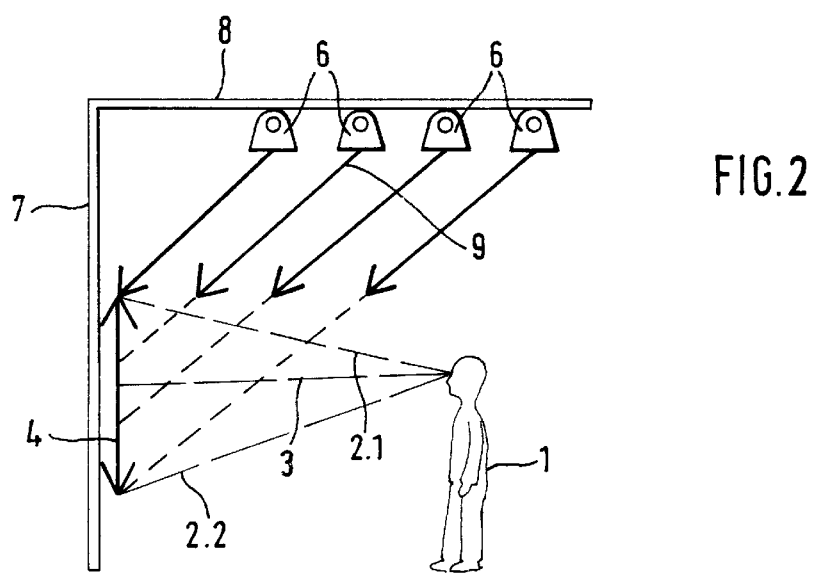

In FIG. 1 and FIG. 2 is shown a first arrangement of the apparatus for measurement and visual matching, which can be constructed as a light booth or can be contained in a room. In both cases a vertical wall 7 and a ceiling 8 form the boundary walls of the light booth or room. On the vertical wall 7 is shown a vertically extending area 5 which serves to hold a sample or several samples located adjacent to each other. Means for holding and fixing the samples are not shown in more detail, but are there in a known manner. The sample is slidable up and down on the vertical area 5 according to an arrow 4 indicating the direction of displacement. On the ceiling 8 are mounted lamps 6 which are elongate parallel to the wall, fitted with fluorescent tubes and corresponding reflectors, which are constructed in much a way that they focus narrowly in planes transversely to the respective bulb axis, the main beam plane, and irradiate the vertical area 5 approximately from an angle of 45°, as shown by an arrow 9 indicating the main beam direction.

An observer can look at the samples from different angles. The direction 3 indicates a basic position from the direction of the normal, i.e. perpendicularly to the sample surface, a direction 2.1 defines an angle of up to 30° to the normal on the sample or 15° of the luminosity or gloss and a direction of observation 2.2 in turn gives an angle of 30° to the normal or 75° of the luminosity, wherein 0° of the luminosity means looking into the lamps directly via the reflective surface of the sample.

Usually the samples, e.g. sample to be matched and reference sample, are mounted in such a way that the observer 1 views the samples according to direction 3 as the basic position. Then they are displaced along the path of displacement 4 and viewed again. After displacement the samples are in each case illuminated always from the same direction by the lamps 6 and with the same illuminance as before, with the result that if occasion arises matching errors of the sample compared with the reference sample can be detected precisely and reliably. Naturally only one sample or a plurality of samples can be viewed.

Figure 3:
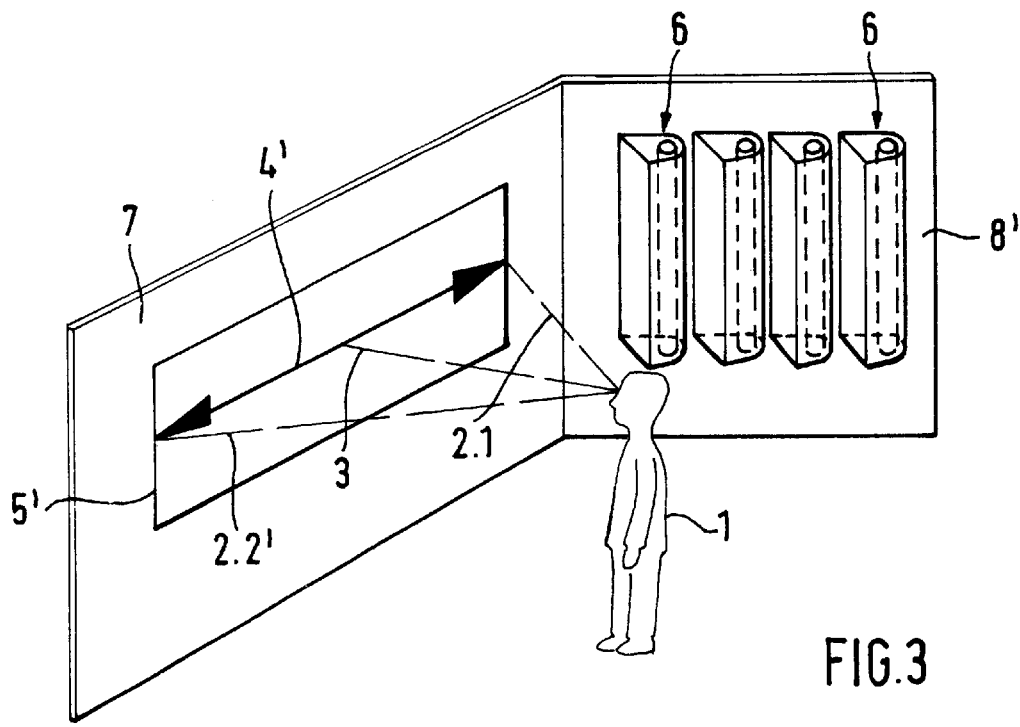
Figure 4:
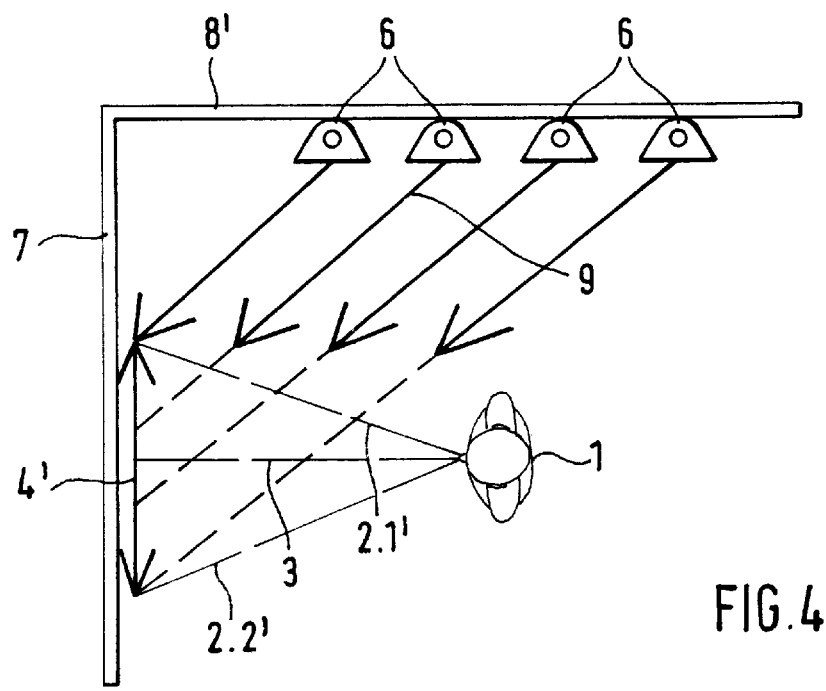

In FIGS. 3 and 4 a further embodiment is shown, in which samples are arranged on a horizontally extending area 5' and are correspondingly displaceable according to a horizontal direction of displacement. On displacement the sample is illuminated over the whole surface 5' always from the same direction by the lamps 6, which in this embodiment are mounted on an additional side wall 8' parallel to the wall 7 and oriented vertically. In planes transversely to the bulb axis, that is, in a horizontal plane, the main beam plane, the lamps focus narrowly and irradiate the sample approximately from an angle of 45°. The observer 1 can look at the sample from different angles, direction 3 perpendicular to the sample surface, direction 2.2' at an angle of up to 30° to the normal on the sample or 75° of the luminosity, and the direction 2.1' again 30° to the normal or 15° of the luminosity.

In other respects the arrangement and manner of operation correspond to those according to FIGS. 1 and 2.

Instead of the observer 1 an electronic and/or electrooptical detection and measurement device can be provided, by which the color of the sample is measured directly.

In the embodiments described the lamps 6 are mounted stationarily on the ceiling 8 or side wall 8'. They may however be displaced with constant geometrical coordination with the sample or samples.

What is claimed is:

1. Apparatus for the measurement or visual matching of the color or color effects of a flat or slightly curved surface element as part of the surface of a sample, in which the sample is displaceable with the surface element in a plane along a straight line perpendicularly to the normal of the surface element, and the surface element can be observed from a fixed location from different directions of observation before and after displacement, and in which a lighting apparatus is provided with which at least the partial surface of the sample which is viewed is illuminated essentially with the same lighting intensity and from the same direction in all positions possible due to the displacements, wherein the light distribution of the lighting apparatus in a plane containing the normal of the surface element and the straight line of displacement has a main beam direction obliquely to the normal of the surface element.

2. Apparatus according to claim 1, characterized in that the light distribution has a main beam direction of 45° to the normal of the surface element.

3. Apparatus according to claim 1, characterized in that one of the directions of observation is perpendicular to the surface element.

4. Apparatus according to claim 1, characterized in that the light distribution of the lighting apparatus focuses narrowly in the plane containing the normal of the surface element and the straight line of displacement.

5. Apparatus according to claim 1, characterized in that the lighting apparatus consists of at least one elongate lamp which is oriented parallel to the plane in which the sample is displaced and perpendicularly penetrates the plane containing the surface normal and the straight line of displacement.

6. Apparatus according to claim 1, characterized in that the lighting apparatus is stationary.

7. Apparatus according to claim 1, characterized in that the lighting apparatus is displaceable with a constant geometrical coordination with the sample.

8. Apparatus according to claim 1, characterized in that the range of displacement of the sample is defined such that, with the fixed location of the observer, all angles of the luminosity needed to assess the samples are adjustable between 15° and 75°.

9. Apparatus according to claim 1, characterized in that at the fixed location is arranged an electronic and/or electrooptical detecting and measuring device, contactless measurement can be performed from the same direction as visual matching.

* * * * *